(12) United States Patent
Emstad et al.

(10) Patent No.: US 7,641,659 B2
(45) Date of Patent: Jan. 5, 2010

(54) SPINAL ACCESS INSTRUMENT

(75) Inventors: Erik E. Emstad, St. Paul, MN (US); Daniel Robbins, North Bennington, VT (US)

(73) Assignee: Zimmer Spine, Inc., Minneapolis, MN (US)

( * ) Notice: Subject to any disclaimer, the term of this patent is extended or adjusted under 35 U.S.C. 154(b) by 1039 days.

(21) Appl. No.: 10/726,329

(22) Filed: Dec. 1, 2003

(65) Prior Publication Data

US 2004/0181231 A1 Sep. 16, 2004

Related U.S. Application Data

(60) Provisional application No. 60/455,062, filed on Mar. 13, 2003.

(51) Int. Cl.
*A61F 5/00* (2006.01)
(52) U.S. Cl. .................. 606/86 R; 606/96; 600/210
(58) Field of Classification Search .................. 606/86, 606/53, 61, 60, 99, 190, 246, 263, 86 A, 86 R, 606/103–104, 323, 96, 198; 600/204, 210, 600/215, 224
See application file for complete search history.

(56) References Cited

U.S. PATENT DOCUMENTS

| | | | | |
|---|---|---|---|---|
| 3,875,595 | A | | 4/1975 | Froning |
| 4,441,492 | A | * | 4/1984 | Rydell et al. ................. 606/67 |
| 4,545,374 | A | * | 10/1985 | Jacobson ..................... 606/61 |
| 4,616,635 | A | * | 10/1986 | Caspar et al. ................ 600/215 |
| 4,620,460 | A | * | 11/1986 | Gonzales, Jr. ............... 81/124.4 |
| 4,862,891 | A | * | 9/1989 | Smith ......................... 606/191 |
| 5,158,543 | A | * | 10/1992 | Lazarus ...................... 604/164.1 |
| 5,176,649 | A | * | 1/1993 | Wakabayashi ........... 604/164.09 |
| 5,357,983 | A | | 10/1994 | Mathews |
| 5,472,426 | A | * | 12/1995 | Bonati et al. ............... 604/164.1 |
| 5,792,044 | A | | 8/1998 | Foley et al. |
| 5,797,936 | A | | 8/1998 | Kleihues |

(Continued)

FOREIGN PATENT DOCUMENTS

EP 0807415 A2 11/1997

(Continued)

OTHER PUBLICATIONS

"Spinal Concepts Launches Access™ Dilation Port for Minimally Invasive Spinal Surgery," *Spinal Concepts—Media Relations, Communications*, http://www.spinalconcepts.com/communications/access_dilation_port_launch.html, 1 page (Date: publicly known prior to Mar. 13, 2003).

(Continued)

*Primary Examiner*—Thomas C Barrett
*Assistant Examiner*—James L. Swiger
(74) *Attorney, Agent, or Firm*—Crompton, Seager & Tufte, LLC.

(57) ABSTRACT

A method of, and surgical instrument for accessing first and second pedicle locations of a spinal column area. The surgical instrument including a blade member slidably positionable along first and second wires. The instrument having a nested arrangement of members, including a portal member having an elongated aperture to access the first and second pedicle locations. The nested arrangement further including a plurality of members configured and sized to incrementally expand the access opening to the spinal column area.

16 Claims, 11 Drawing Sheets

U.S. PATENT DOCUMENTS

| | | | |
|---|---|---|---|
| 5,928,139 A * | 7/1999 | Koros et al. | 600/205 |
| 5,954,671 A * | 9/1999 | O'Neill | 600/567 |
| 5,964,761 A | 10/1999 | Kambin | |
| 5,976,146 A * | 11/1999 | Ogawa et al. | 606/86 |
| 6,063,088 A * | 5/2000 | Winslow | 606/61 |
| 6,159,179 A * | 12/2000 | Simonson | 604/117 |
| 6,175,758 B1 | 1/2001 | Kambin | |
| 6,228,022 B1 | 5/2001 | Friesem et al. | |
| 6,383,191 B1 * | 5/2002 | Zdeblick et al. | 606/105 |
| 6,451,023 B1 * | 9/2002 | Salazar et al. | 606/86 R |
| 6,524,320 B2 * | 2/2003 | DiPoto | 606/108 |
| 6,596,008 B1 | 7/2003 | Kambin | |
| 6,811,558 B2 * | 11/2004 | Davison et al. | 606/190 |
| 7,008,431 B2 * | 3/2006 | Simonson | 606/86 |
| 7,056,329 B2 * | 6/2006 | Kerr | 606/206 |
| 7,074,226 B2 * | 7/2006 | Roehm et al. | 606/90 |
| 7,182,729 B2 * | 2/2007 | Abdelgany et al. | 600/219 |
| 2002/0151921 A1 * | 10/2002 | Kanner et al. | 606/190 |
| 2003/0083688 A1 * | 5/2003 | Simonson | 606/191 |
| 2005/0038440 A1 * | 2/2005 | Larson et al. | 606/86 |

FOREIGN PATENT DOCUMENTS

| | | |
|---|---|---|
| EP | 0890341 A1 | 1/1999 |

OTHER PUBLICATIONS

"Access™ Dilation Port," *Spinal Concepts—Access™ Dilation Port, Products*, http://www.spinalconcepts.com/products/adp.html, 2 pages (Date: publicly known prior to Mar. 13, 2003).

European Patent Office, Communication and European Search Report, Application No. 04251366.3, dated Jul. 27, 2006 (6 pages).

European Patent Office, Communication and Partial European Search Report, Application No. 04251366.3, dated May 22, 2006 (6 pages).

* cited by examiner

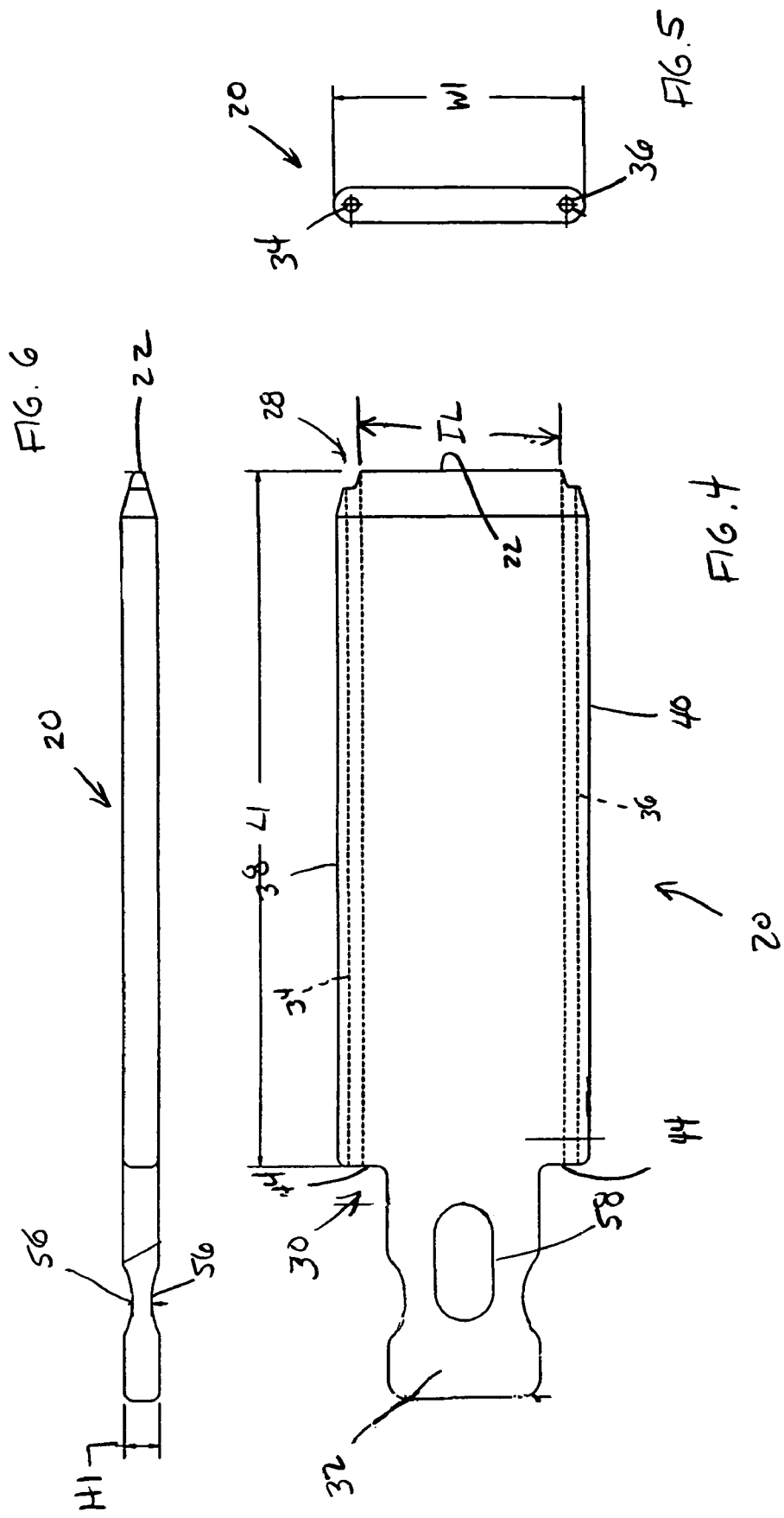

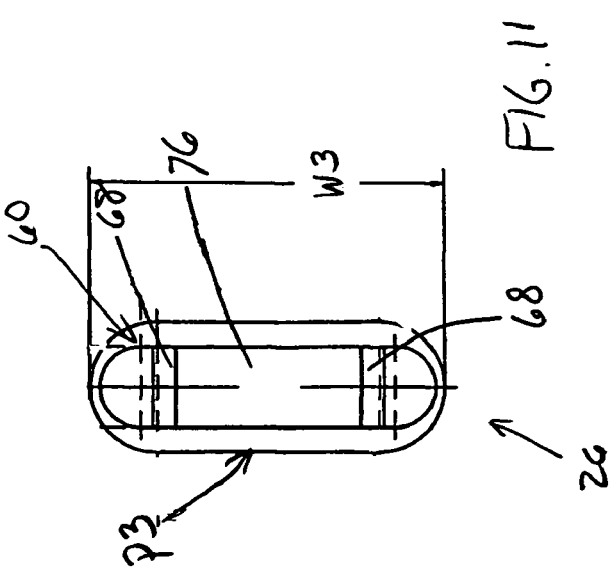
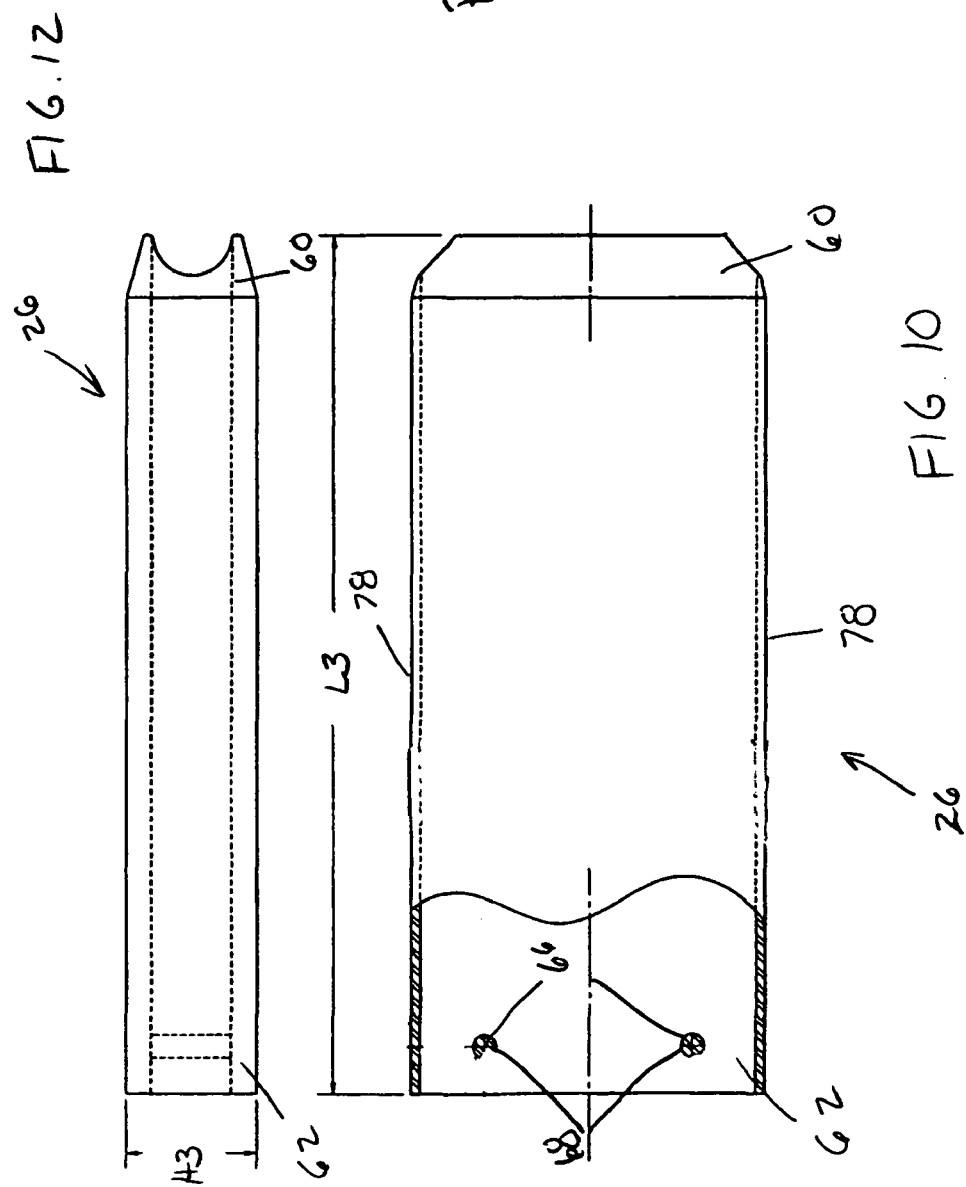

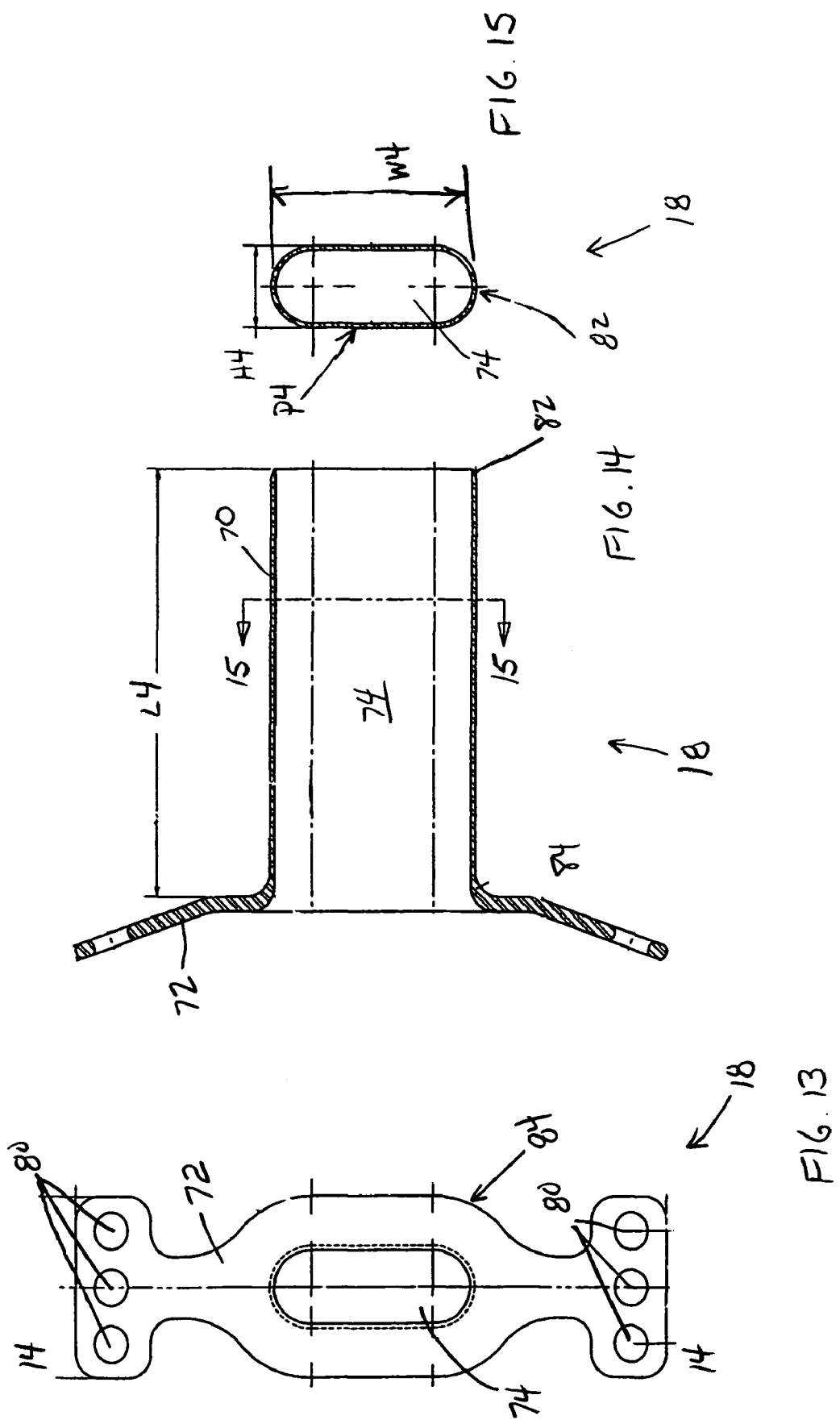

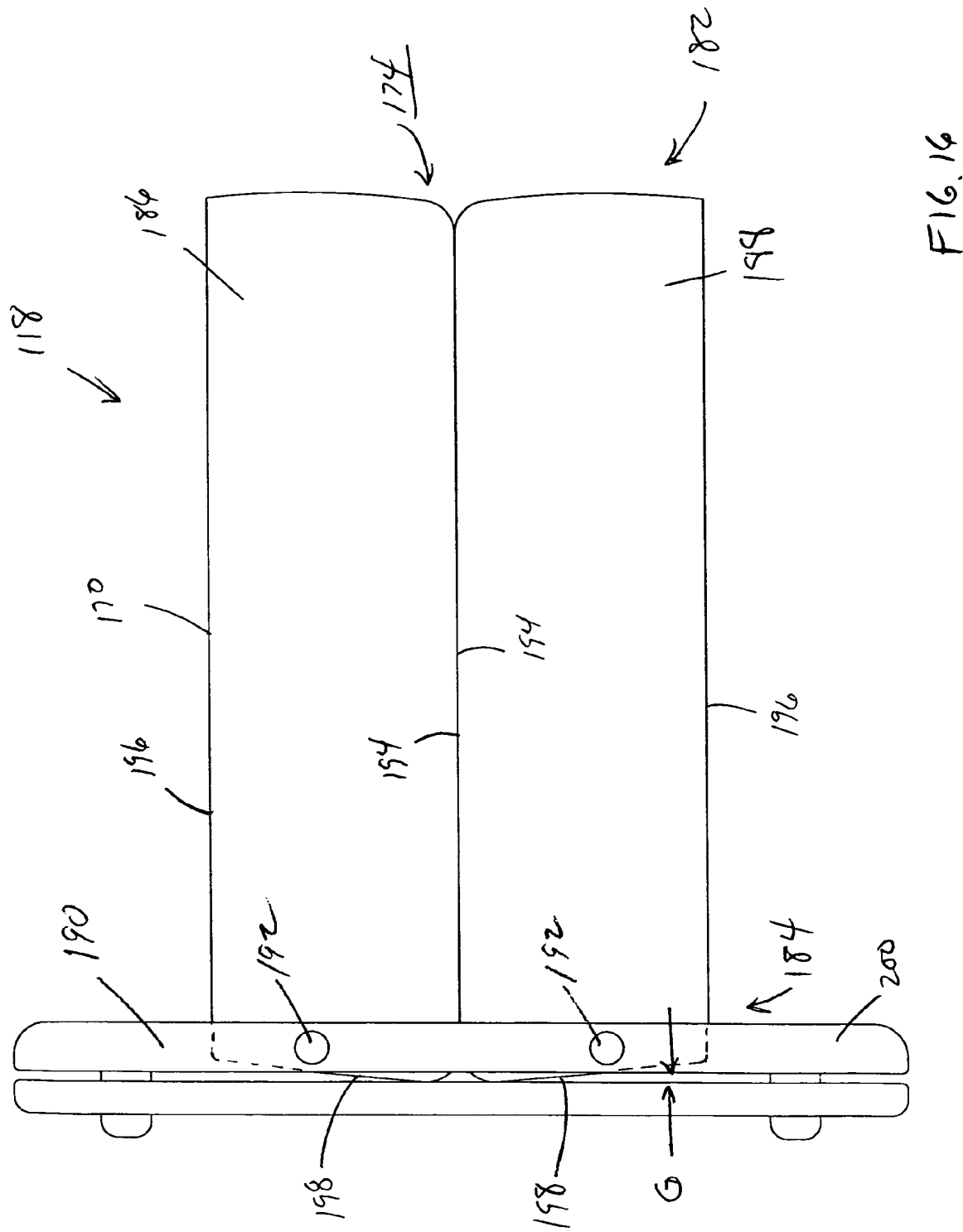

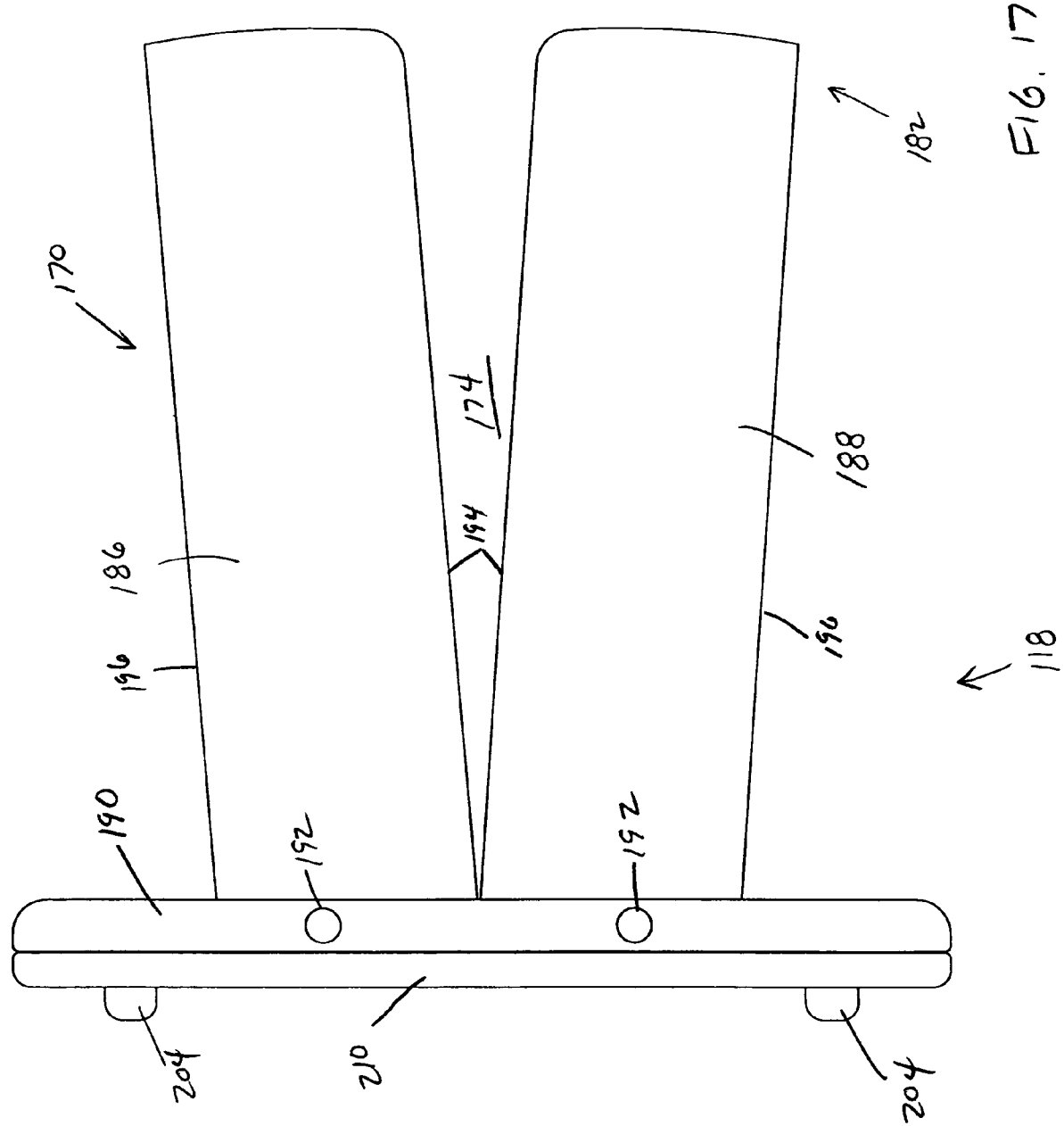

SPINAL ACCESS INSTRUMENT

CROSS-REFERENCE TO RELATED APPLICATIONS

This application claims the benefit of U.S. Provision Application No. 60/455,062, filed on Mar. 13, 2003; which application is incorporated herein by reference.

TECHNICAL FIELD

This disclosure relates generally to methods and devices for accessing an area of a patient's spinal column during a surgical procedure. More particularly, this disclosure relates to an instrument that provides an access opening to the spinal column.

BACKGROUND

A wide variety of surgical techniques have been used to access the spinal column in spinal surgery procedures. For example, some techniques included making an incision in the patient's back and distracting or separating tissue and muscle to expose a wide area of the spine in order to perform the spinal surgery procedure. Such techniques often result in excessive invasions into the patient's spine and back region causing major damage to the normal anatomy, and significant and dangerous blood loss.

In an attempt to minimize risks associated with spinal surgery procedures, some surgical techniques have been developed wherein only portions of the spinal column area are accessed during various stages of the surgical procedure. In these procedures, a smaller incision can be used to access the portion of the spinal column area. However, access to only a portion of the spinal column area does not provide sufficient access for all surgical procedures.

In general, improvement has been sought with respect to such surgical techniques, generally to better provide sufficient accessibility to a spinal column area while minimizing anatomical trauma and blood loss.

SUMMARY

One aspect of the present disclosure relates to a surgical instrument for accessing first and second pedicle locations of a spinal column. The surgical instrument includes a portal member having an elongated aperture. The elongated aperture of the portal member is sized to provide simultaneous access to each of the first and second pedicle locations. The instrument also includes a placement wire and a blade member. The blade member is positionable over the placement wire and is positionable within the elongated aperture of the portal member.

Another aspect of the present disclosure relates to a surgical instrument including a first wire, a second wire, and an incremental opening arrangement. The incremental opening arrangement includes a plurality of nested members, including at least a dissector member slidably positionable along the first and second wires and a sleeve member slidably positionable of the dissector member.

Still another aspect of the present disclosure relates to a surgical instrument for accessing first and second pedicle locations including a first wire and a nested arrangement. The nested arrangement includes a blade member slidably positionable over the first wire and configured to provide an incisional opening, and an outer portal member configured to slide over the blade member for introduction into the incisional opening. The outer portal member has an elongated access aperture having a longitudinal dimension that corresponds to the distance between the first and second pedicle locations.

Yet another aspect of the present disclosure relates to a method of accessing the firs and second pedicle sites at a spinal column area incorporated the use of the presently described surgical instrument.

A variety of examples of desirable product features or methods are set forth in part in the description that follows, and in part will be apparent from the description, or may be learned by practicing various aspects of the disclosure. The aspects of the disclosure may relate to individual features as well as combinations of features. It is to be understood that both the foregoing general description and the following detailed description are explanatory only, and are not restrictive of the claimed invention.

BRIEF DESCRIPTION OF THE DRAWINGS

FIG. 4 is a top plan view of one embodiment of a blade member according to the principals of the present disclosure, and shown in FIG. 3;

FIG. 5 is a front elevational view of the blade member of FIG. 4;

FIG. 6 is a side elevational view of the blade member of FIG. 4;

FIG. 10 is top plan view of one embodiment of an intermediate portal member according to the principals of the present disclosure, and shown in FIG. 3;

FIG. 11 is a front elevational view of the intermediate portal member of FIG. 10;

FIG. 12 is a side elevational view of the intermediate portal member of FIG. 10;

FIG. 13 is a rear elevational view of one embodiment of an outer portal member according to the principals of the present disclosure, and shown in FIG. 3;

FIG. 14 is a cross-sectional view of the outer portal member of FIG. 13, taken along line 14-14;

FIG. 15 is a cross-sectional view of the outer portal member of FIG. 14, taken along line 15-15;

FIG. 16 is a top plan view of another embodiment of an outer portal member according to the principals of the present disclosure, shown in a retracted position;

FIG. 17 is a top plan view of the outer portal member of FIG. 16, shown in a distended position;

DETAILED DESCRIPTION

Reference will now be made in detail to various features of the present disclosure that are illustrated in the accompanying drawings. Wherever possible, the same reference numbers will be used throughout the drawings to refer to the same or like parts.

FIGS. 1-18 illustrate surgical instrument embodiments having features that are examples of how inventive aspects in accordance with the principals of the present disclosure may be practiced. Preferred features of the embodiments are adapted for providing a sufficient access opening to a spinal column area while minimizing risks associated with spinal surgery, such as incisional invasiveness, trauma, and blood loss.

Figure 1:
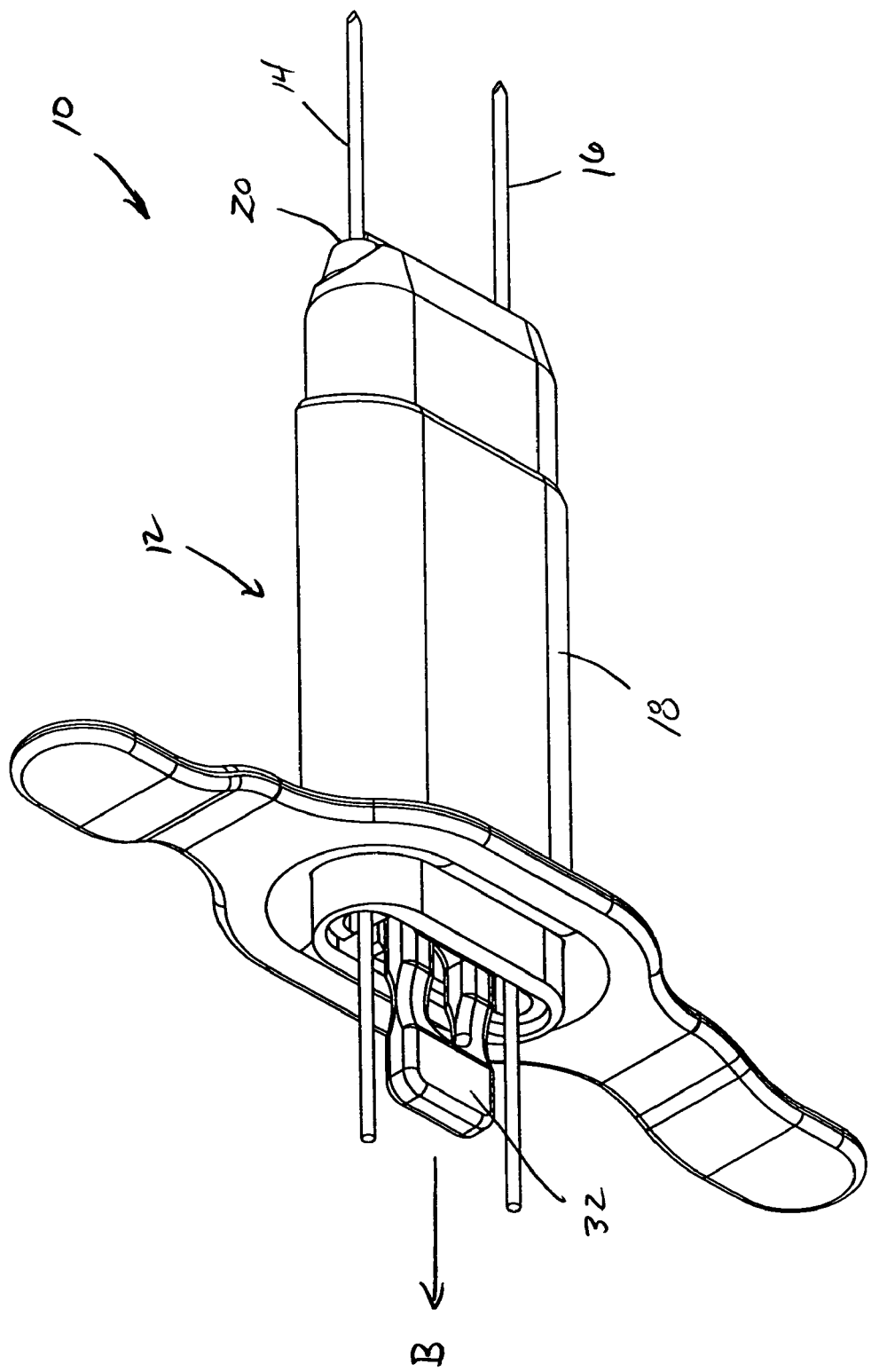
FIG. 1 is a perspective view of one embodiment of a surgical instrument according to the principals of the present disclosure, shown in a nested configuration.

Referring to FIG. 1, one embodiment of the spinal access instrument 10 is illustrated in complete assembly. The spinal access instrument is used to dissect skin tissue and muscle and provide a sufficiently sized opening for accessing a patient's spinal column. A sufficiently sized opening is an opening that is large enough to perform the desired surgical procedure. Preferably the opening provides access to a spinal column area or region such that the surgical procedure can be performed without having to provide more than one incision or opening.

Figure 20:
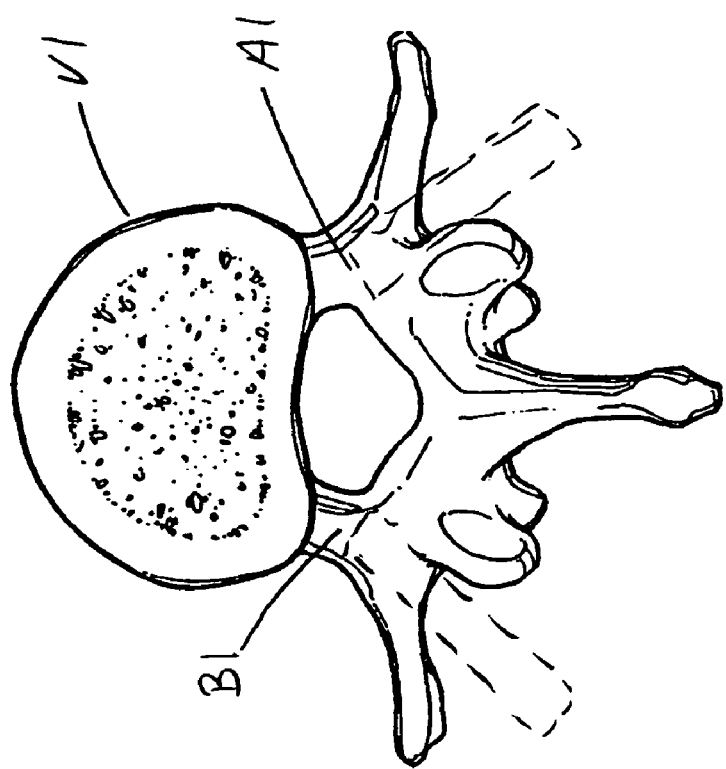
FIG. 20 is a top plan view of one of the two vertebrae of FIG. 19.
Figure 19:
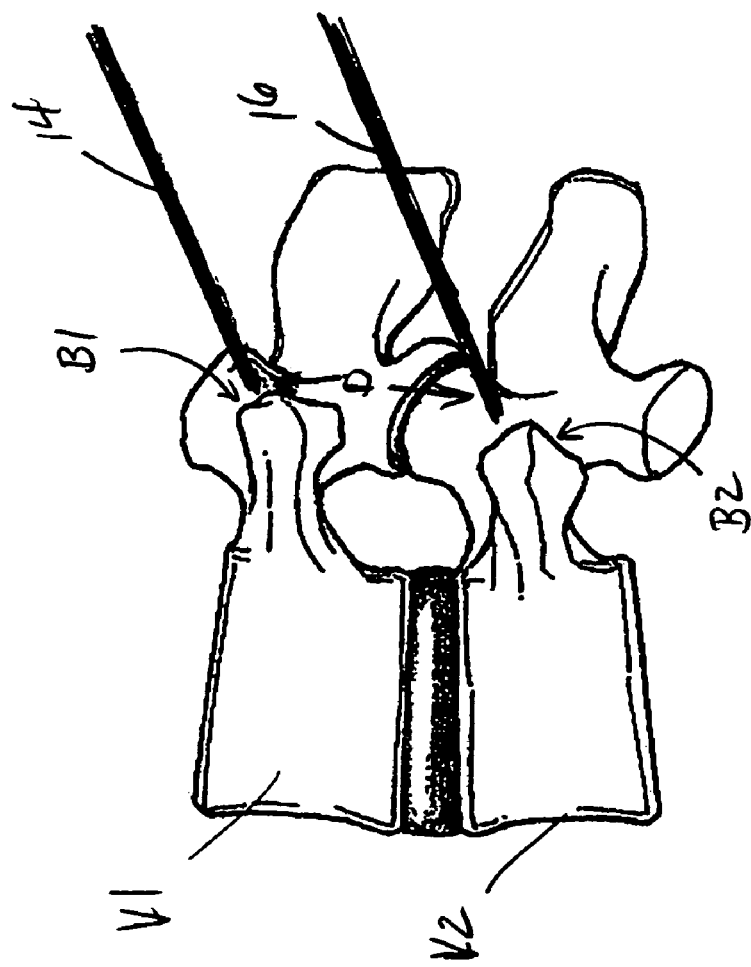
FIG. 19 is a side elevational view two vertebrae.

For example, when performing a spinal procedure involving placement of pedicle screws (schematically represented in FIG. 20 by dashed lines), preferably the accessed spinal column area or region includes first and second pedicle sites. As shown in FIGS. 19 and 20, the first and second pedicle sites or locations are the two sites (A1, A2 (hidden) or B1, B2) that are vertically aligned on upper and lower vertebral bodies V1, V2. That is, the access opening is preferably sized to provide access to the spinal column area including both the first pedicle site (e.g. B1) and the second pedicle site (e.g. B2) of two adjacent vertebrae.

Figure 2:
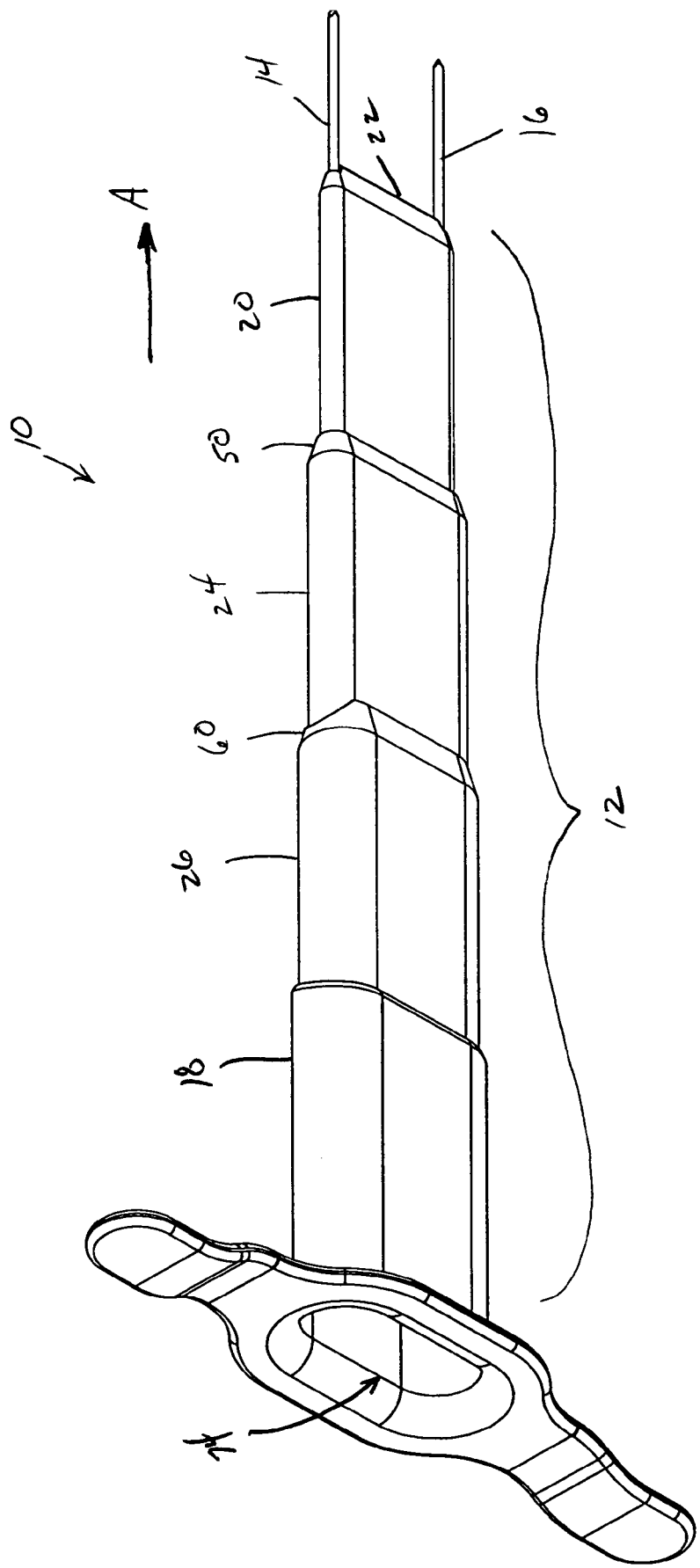
FIG. 2 is a perspective view of the surgical instrument of FIG. 1, shown partially exploded.
Figure 3:
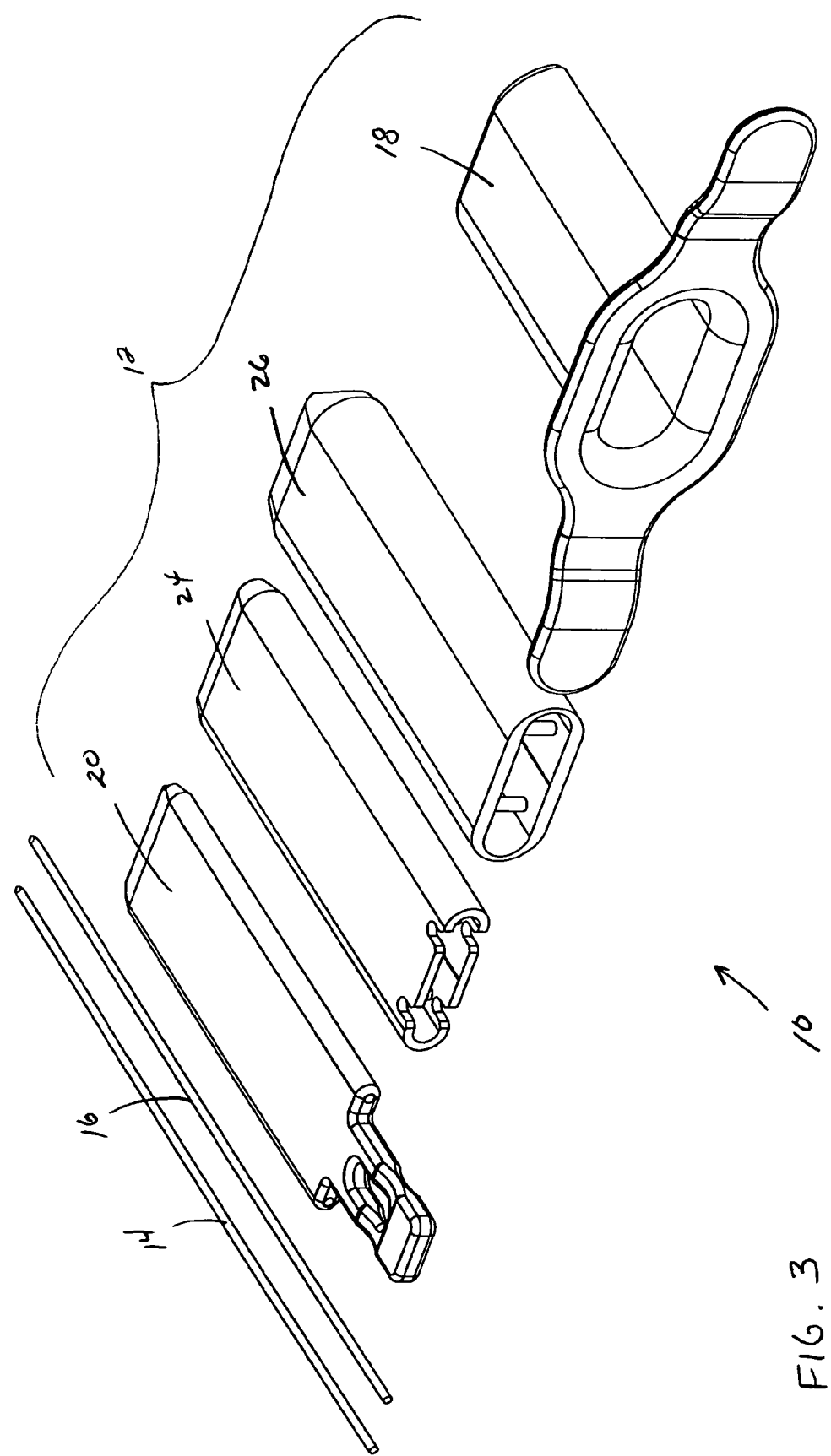
FIG. 3 is a perspective view of the components of the surgical instrument of FIG. 2, shown disassembled.

Referring back to FIG. 1, the surgical instrument 10 generally includes a nested arrangement 12, a first guide or placement wire 14, and a second guide or placement wire 16. As shown in FIGS. 2 and 3, the nested arrangement 12 of the spinal access instrument 10 includes a plurality of components or members sized so that each member fits with the other members in a nested configuration (as shown in FIG. 1). In the nested configuration, each of the members at least partially contains or is at least partially contained within the other members. The plurality of nested members includes at least one portal member (18, 24 or 26) and a dissector or blade member 20. As will be discussed in greater detail, the blade member 20 is used to provide an initial incision and the portal member provides access to the spinal column area through the incision.

Preferably the nested arrangement 12 is configured to incrementally provide an access opening to the spinal column area. What is meant by "incrementally provide an access opening" is that the arrangement provides an initial opening, and thereafter can be used to expand the opening (i.e. increase the cross-sectional area of the opening) as needed. By incrementally expanding the opening, surgical trauma and blood loss is minimized. In contrast, some existing procedures involve making an incision much wider than the incision needed by the present disclosure. The wider incision is needed in some existing procedures so that the skin tissue and muscle can be separated or pulled apart to adequately expose the spinal column area. This excessive invasion often results in anatomical trauma to the tissue or muscle and high blood loss.

In the illustrated embodiment of FIGS. 2 and 3, the nested arrangement 12 includes the blade member 20, and second, third, and fourth sleeve members 24, 26, and 18; although any number of sleeve members can be used in accord with the present disclosure. The second sleeve member or inner portal member 24 is slidably positionable over the blade member 20. The second sleeve member 24 is sized to expand the area of initial incision created by the blade member 20 to a second opening area. The second opening area is generally defined by the outer perimeter of the second sleeve member 24. The third sleeve member or intermediate portal member 26 is slidably positionable over the second sleeve member 24. The third sleeve member 26 is sized and configured to expand the access opening from the second opening area defined by the second sleeve member 24 to a third opening area. The third opening area is generally defined by the outer perimeter of the third sleeve member 26. Finally, the fourth sleeve member or outer portal member 18 is slidably positionable over the third sleeve member 26. The outer portal member 26 is sized and configured to expand the access opening from the third opening area defined by the third sleeve member 26 to a final opening area. The final opening area is generally defined by the outer perimeter of the outer portal member 18.

Referring now to FIGS. 4-6, the blade member 20 of the surgical instrument 10 includes a first end 28 and a second end 30. The first end 28 of the blade member 20 is typically a solid construction defining a blade edge 22. The blade edge 22 is configured to provide an initial incision of length IL (FIG. 4) in the skin tissue and muscle of a patient. A handle 32 is located at the second end 30 opposite the first end 28 of the blade member 20. As shown in FIGS. 4 and 6, the handle includes recessed areas 56 and an aperture 58 for gripping. The handle 32 can include a variety of shapes and geometries configured for gripping and moving the blade member 20 during use.

In general, the blade member 20 has an overall width W1, an overall height H1, and an overall length L1, although the disclosed principles can be applied in a variety of sizes and applications. The width W1 of the blade member 20 is shown in FIG. 5, and is preferably between 19 mm and 58 mm (0.75 inches and 2.25 inches); more preferably between 38 mm and 45 mm (1.5 inches and 1.75 inches). The height H1 of the blade member 20 is shown in FIG. 6, and is preferably between 4 mm and 10 mm (0.175 inches and 0.375 inches); more preferably between 5 mm and 7 mm (0.200 inches and 0.250 inches). The length L1 of the blade member 20 is generally defined between the first end 28 and the second end 30 of the blade member 20, excluding the handle 32. The length L1 of the blade member 20 is preferably between 88 mm and 140 mm (3.5 inches and 5.5 inches); more preferably between 101 mm and 127 mm (4.0 inches and 5.0 inches).

As shown in FIGS. 4 and 5, the blade member 20 includes first and second apertures 34, 36 extending along the length L1 of the blade member 20. The first and second aperture 34, 36 are offset from edges 38, 40 of the blade member 20 and extend from the first end 28 to the second end 30 of the blade member 20. Each of the first and second apertures 34, 36 is sized and configured for receipt of the corresponding first and second placement wires 14, 16 (FIG. 2). In the illustrated embodiment, the first and second placement wires 14, 16 are approximately 2 mm (0.08 inches) in diameter; correspondingly the first and second apertures 34, 36 are approximately 2.3 mm (0.09 inches) in diameter.

Figure 8:
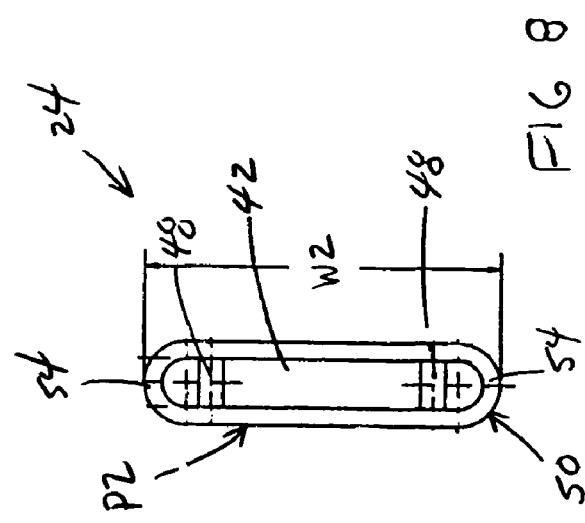
FIG. 8 is a front elevational view of the inner portal member of FIG. 7.
Figure 9:
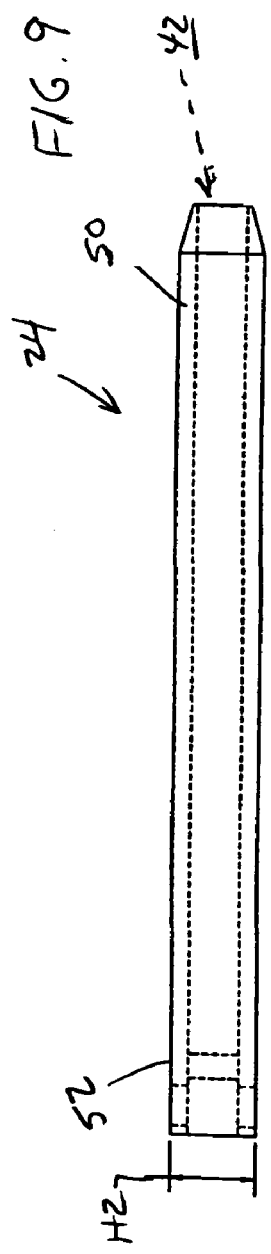
FIG. 9 is a side elevational view of the inner portal member of FIG. 7.
Figure 7:
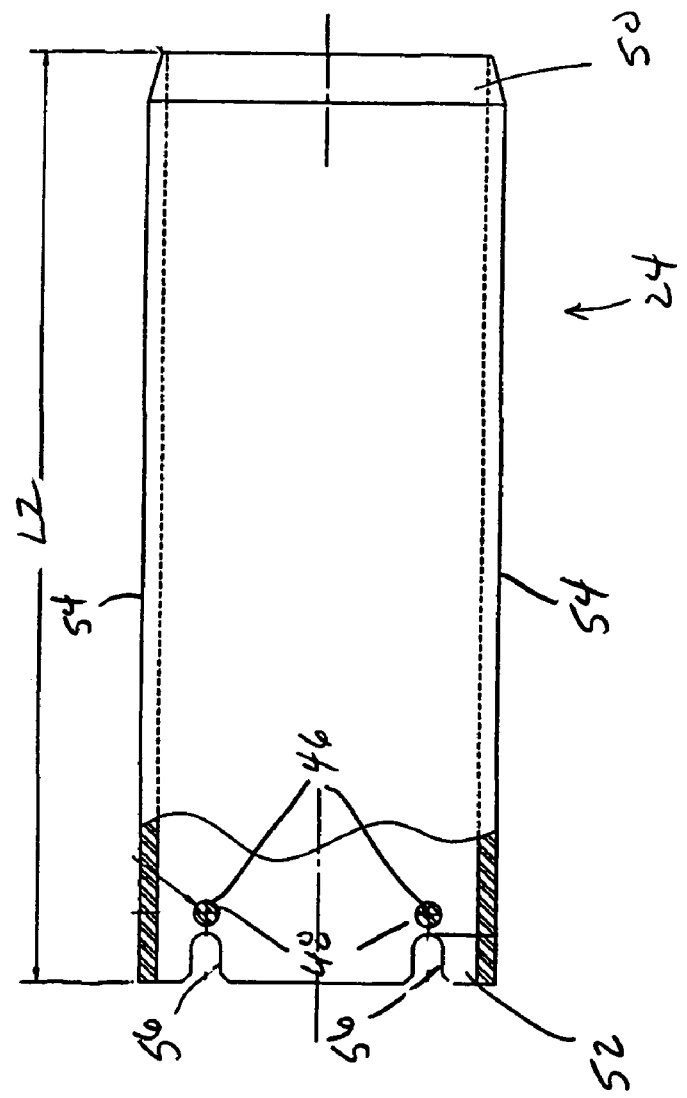
FIG. 7 is a top plan view of one embodiment of an inner portal member according to the principals of the present disclosure, and shown in FIG. 3.

Referring now to FIGS. 7-9, the second sleeve member or inner portal member 24 of the nested arrangement 12 is illustrated. The second sleeve member 24 is generally a tubular construction having a first end 50 and a second end 52. The tubular construction of the second sleeve member defines an elongated aperture 42 sized and configured for receipt of the blade member 20. In particular, the second sleeve member 24 fits over the handle and slides along the blade member to nest with or cover the blade member 20. The first end 50 of the second sleeve member 24 is tapered. In use, the tapered first end 50 assists in gradually expanding the access opening from the initial area of the incision created by the blade member 20 to the second opening area defined by the outer perimeter P2 (FIG. 8) of the second sleeve member 24.

The second sleeve member 24 is configured to slide over the blade member 20 until shoulders 44 (FIG. 4) of the blade member 20 contact stop structures 46 of the second sleeve member 24. In the illustrated embodiment, the stop structures 46 include pins 48 positioned within the elongated aperture 42. The pins 48 are positioned adjacent to the second end 52 of the second sleeve member 24. Each of the pins 48 is offset from sidewalls 54 of the second sleeve member 24 so that when assembled as shown in FIGS. 1 and 2, the first and second placement wires 14, 16 extend between the pins 48 and the sidewalls 54 of the second sleeve member 24.

In general, the second sleeve member 24 has an overall width W2, an overall height H2, and an overall length L2, although the disclosed principles can be applied in a variety of sizes and applications. The width W2 of the second sleeve member 24 is shown in FIG. 8, and is preferably between 24 mm and 63 mm (0.95 inches and 2.45 inches); more preferably between 43 mm and 50 mm (1.70 inches and 1.95 inches). The height H2 of the second sleeve member 24 is shown in FIG. 9, and is preferably between 9 mm and 15 mm (0.375 inches and 0.575 inches); more preferably between 10 mm and 12 mm (0.400 inches and 0.450 inches). The length L2 of the second sleeve member 24 is generally defined between the first end 50 and the second end 52 of the second sleeve member 24. The length L2 of the second sleeve member is preferably between 95 mm and 146 mm (3.75 inches and 5.75 inches); more preferably between 107 mm and 134 mm (4.25 inches and 5.25 inches). The outer perimeter P2 of the second sleeve member 24 defines the second access opening area; the second access opening area is generally between 180 and 716 square mm (0.28 and 1.11 square inches).

Referring now to FIGS. 10-12, the third sleeve member or intermediate portal member 26 of the nested arrangement 12 is illustrated. The third sleeve member 26 is also generally a tubular construction having a first end 60 and a second end 62. The tubular construction of the third sleeve member 26 defines an elongated aperture 76 sized and configured for receipt of the second sleeve member 24. In particular, the third sleeve member 26 fits over the second sleeve member 24 to nest with or cover the second sleeve member 24. Similar to the second sleeve member, the first end 60 of the third sleeve member is tapered to assist in gradually expanding the access opening from the second opening area to the third opening area defined by the outer perimeter P3 of the third sleeve member 26.

The third sleeve member 26 slides over the second sleeve member 24 until notches 56 (FIG. 7) of the second sleeve member 24 contact stop structures 66 of the third sleeve member 26. In the illustrated embodiment, the stop structures 66 include pins 68 positioned within the elongated aperture 76. The pins 68 are positioned adjacent to the second end 62 of the third sleeve member 26. Each of the pins 68 is offset from sidewalls 78 of the third sleeve member 26 so that when assembled as shown in FIG. 2, the first and second placement wires 14, 16 extend between the pins 68 and the sidewalls 78 of the third sleeve member 26.

In general, the third sleeve member 24 has an overall width W3, an overall height H3, and an overall length L3, although the disclosed principles can be applied in a variety of sizes and applications. The width W3 of the third sleeve member 26 is shown in FIG. 11, and is preferably between 27 mm and 66 mm (1.08 inches and 2.58 inches); more preferably between 46 mm and 53 mm (1.83 inches and 2.08 inches). The height H3 of the third sleeve member 26 is shown in FIG. 12, and is preferably between 17 mm and 23 mm (0.675 inches and 0.875 inches); more preferably between 17 mm and 19 mm (0.700 inches and 0.750 inches). The length L3 of the third sleeve member 26 is generally defined between the first end 60 and the second end 62 of the third sleeve member 26. The length L3 of the third sleeve member is preferably between 95 mm and 146 mm (3.75 inches and 5.75 inches); more preferably between 107 mm and 134 mm (4.25 inches and 5.25 inches). The outer perimeter P3 of the third sleeve member 26 defines the third access opening area; the third access opening area is generally between 368 and 1148 square mm (0.57 and 1.78 square inches).

Referring now to FIGS. 13-15, the fourth sleeve member or outer portal member 18 of the nested arrangement 12 is illustrated. The outer portal member 18 generally includes a sleeve portion 70 having a first end 82 and a second end 84. The sleeve portion 70 defines an elongated aperture 74 that extends from the first end 82 to the second end 84.

A handle portion 72 of the outer portal member 18 is located at the second end 84 of the sleeve portion 70. The handle portion 72 can include a plurality of holes 80. The holes 80 provide locations at which other surgical tools (not shown) can be attached for use during the surgical procedure.

In general, the outer portal member 18 has an overall width W4, an overall height H4, and an overall length L4, although the disclosed principles can be applied in a variety of sizes and applications. The width W4 of the outer portal member 18 is shown in FIG. 15, and is preferably between 30 mm and 68 mm (1.19 inches and 2.69 inches); more preferably between 49 mm and 56 mm (1.94 inches and 2.19 inches). The height H4 of the outer portal member 18 is also shown in FIG. 15, and is preferably between 20 mm and 25 mm (0.787 inches and 0.987 inches); more preferably between 20 mm and 22 mm (0.812 inches and 0.862 inches). The length L4 of the outer portal member 18 is generally defined between the first end 82 and the second end 84 of the outer portal member 18. The length L4 of the outer portal member is preferably between 97 mm and 149 mm (3.85 inches and 5.85 inches); more preferably between 110 mm and 136 mm (4.35 inches and 5.35 inches). The outer perimeter P4 of the outer portal member 18 defines the fourth or final access opening area; the fourth or final access opening area is generally between 477 and 1348 square mm (0.74 and 2.09 square inches).

In use, the surgical access instrument 10 provides access to first and second pedicle sites at a spinal column area or region. To begin a procedure, the first placement wire 14 is advanced through a patient's skin tissue and muscle until the wire 14 is positioned at a selected first pedicle site (e.g. B1 in FIG. 19) of a first vertebral body V1. The second placement wire 16 is positioned at a corresponding upper or lower second pedicle site (e.g. B2 in FIG. 19) of an adjacent vertebral body V2. The first and second pedicle sites are located a general distance D apart from one another. The site of the access opening is located at the region defined generally between and adjacent to the first and second placement wires 14, 16.

While first ends of the first and second placement wires 14, 16 are positioned at the first and second pedicle locations, opposite ends of the placement wires 14, 16 are inserted within the first and second apertures 34, 36 at the first end 28 of the blade member 20. The blade member 20 slides along the first and second placement wires 14, 16 in a first direction (represented by arrow A in FIG. 2) until the blade member 20 is adjacent to the skin tissue located between the first and second placement wires 14, 16. As the blade member 20 is further advanced toward the first and second pedicle sites, the blade edge 22 provides an initial incision through the skin tissue and muscle to the spinal column area. The surgeon can use hand force or a tapping hammer, for example, to advance the blade member along the placement wires 14, 16 to a desired depth.

When the blade member 20 is position at the desired depth adjacent to the spinal column area, the first end 50 of the second sleeve member 24 is positioned over the second end 30 of the blade member 20 (FIG. 2). The second sleeve member 24 slides along the blade member 20 in the first direction A until the second sleeve member 24 is adjacent to the initial incision in the skin tissue. As the second sleeve member 24 is further advanced toward the spinal column area, the tapered first end 50 of the second sleeve member 24 is introduced into the initial incision and begins to enlarge the incisional area. The incisional area is incrementally enlarged to the second opening area defined by the outer perimeter of the second sleeve member 24.

The second sleeve member 24 is inserted to a desired depth adjacent to the spinal column area, however cannot be inserted a depth exceeding the depth of the blade member 20. That is, the stop structures 46 of the second sleeve member 24 contact the shoulders 44 of the blade member 20 to limit the insertion depth of the second sleeve member.

When the second sleeve member 24 is position at the desired depth adjacent to the spinal column area, the first end 60 of the third sleeve member 26 is positioned over the second end 52 of the second sleeve member 24 (FIG. 2). The third sleeve member 26 slides along the second sleeve member 24 in the first direction A until the third sleeve member 26 is adjacent to the access opening in the skin tissue. As the third sleeve member 26 is further advanced toward the spinal column area, the tapered first end 60 of the third sleeve member 26 is introduced into the access opening and begins to enlarge the access opening. The access opening is incrementally enlarged from the second opening area to the third opening area defined by the outer perimeter of the third sleeve member 26.

The third sleeve member 26 is inserted to a desired depth adjacent to the spinal column area, however cannot be inserted a depth exceeding the depth of the second sleeve member 24. That is, the stop structures 66 of the third sleeve member 26 engage the notches 56 of the second sleeve member 24 to limit the insertion depth of the third sleeve member 26.

Similar to the preceding steps, when the third sleeve member 26 is position at the desired depth adjacent to the spinal column area, the first end 82 of the outer portal member 18 is positioned over the second end 62 of the third sleeve member 26 (FIG. 2). The outer portal member 18 slides along the third sleeve member 26 in the first direction A until the outer portal member 18 is adjacent to the access opening in the skin tissue. As the outer portal member 18 is further advanced toward the spinal column area, the first end 82 of the outer portal member 18 is introduced into access opening and begins to enlarge the access opening. The access opening is incrementally enlarged from the third opening area to the final opening area defined by the outer perimeter of the outer portal member 18.

When the portal member 18 has been positioned at the desired depth adjacent to the spinal column area, each of the members 18, 20, 24, and 26 are in the nested configuration, generally shown in FIG. 1. The access opening to the first and second pedicle sites at the spinal column area has been incrementally expanded to minimized incisional trauma and blood loss.

To continue the surgical procedure, each of the blade member 20, the second sleeve member 24, and the third sleeve member 26, is removed from the elongated aperture 74 of the portal member 18. Removing all three members 20, 24, and 26 can be accomplished by simply grasping the handle 32 of the blade member 20 and pulling the blade member 20 out from the aperture 74 of the outer portal member 18.

In particular, each of the blade, second sleeve and third sleeve members 20, 24, 26 are interconnected when moved in a second direction B (FIG. 1) relative to the outer portal member 18. That is, the shoulders 44 of the blade member 20 contact the pins 48 of the second sleeve member 24, and the notches 56 of the second sleeve member 24 engage the pins 68 of the third sleeve member 26 to form an interconnection that permits all three nested members 20, 24, 26 to be simultaneously removed from the aperture 74 of the outer portal member 18. Thus, as a surgeon pulls the blade member 20 from the aperture 74, the blade member 20 interconnects with the second sleeve member 24 and the second sleeve member interconnects with the third sleeve member 26 so that the three nested and interconnected members 20, 24, 26 can be removed at the same time.

When the three nested members 20, 24, and 26, are removed from the elongated aperture 74 of the outer portal member 18, the surgeon now has access to first and second pedicle sites at the spinal column area. The access is provided through the elongated aperture 74; thereby the elongated aperture 74 of the outer portal member 18 is sized and configured to correspond to the distance (D) between the first and second pedicle sites. More preferably, the elongated aperture 74 provides access to each of the first and second pedicle sites and the immediate surrounding area of each pedicle site at the spinal column area. In the illustrated embodiment, the elongated aperture 74 is sized and configured to receive and guide pedicle screws into the first and second vertebral bodies at the first and second pedicle sites.

It is to be understood that the placement wires 14, 16 may or may not be removed from the elongated aperture 74 with the three nested members 20, 24, 26. In some procedures, pedicle screws having a bore extending through the screw shaft are positioned on the placement wires. The placement wires therein act as guide wires to direct the pedicle screws to the first and second pedicle sites. In other procedures, the first and second placement wires 14, 16 are removed with the three nested members 20, 24, 26 and the screws are engaged by an appropriate driving tool and positioned down into the aperture to the first and second pedicle sites. In yet another alternative, the placement wires 14, 16 can be removed from the blade member 20 after the blade member 20 has been properly positioned adjacent to the spinal column area.

The pedicle screws can include a variety of pedicle screw configurations known in the art. Typically the diameter of pedicle screws range between about 5 mm and 8 mm. These specific dimensions are merely illustrative of normal configurations and can be varied as needed. Accordingly, the elongated aperture 74 of the outer portal member 18 can be varied to accommodate the variety of pedicle screw configurations.

Figure 18:
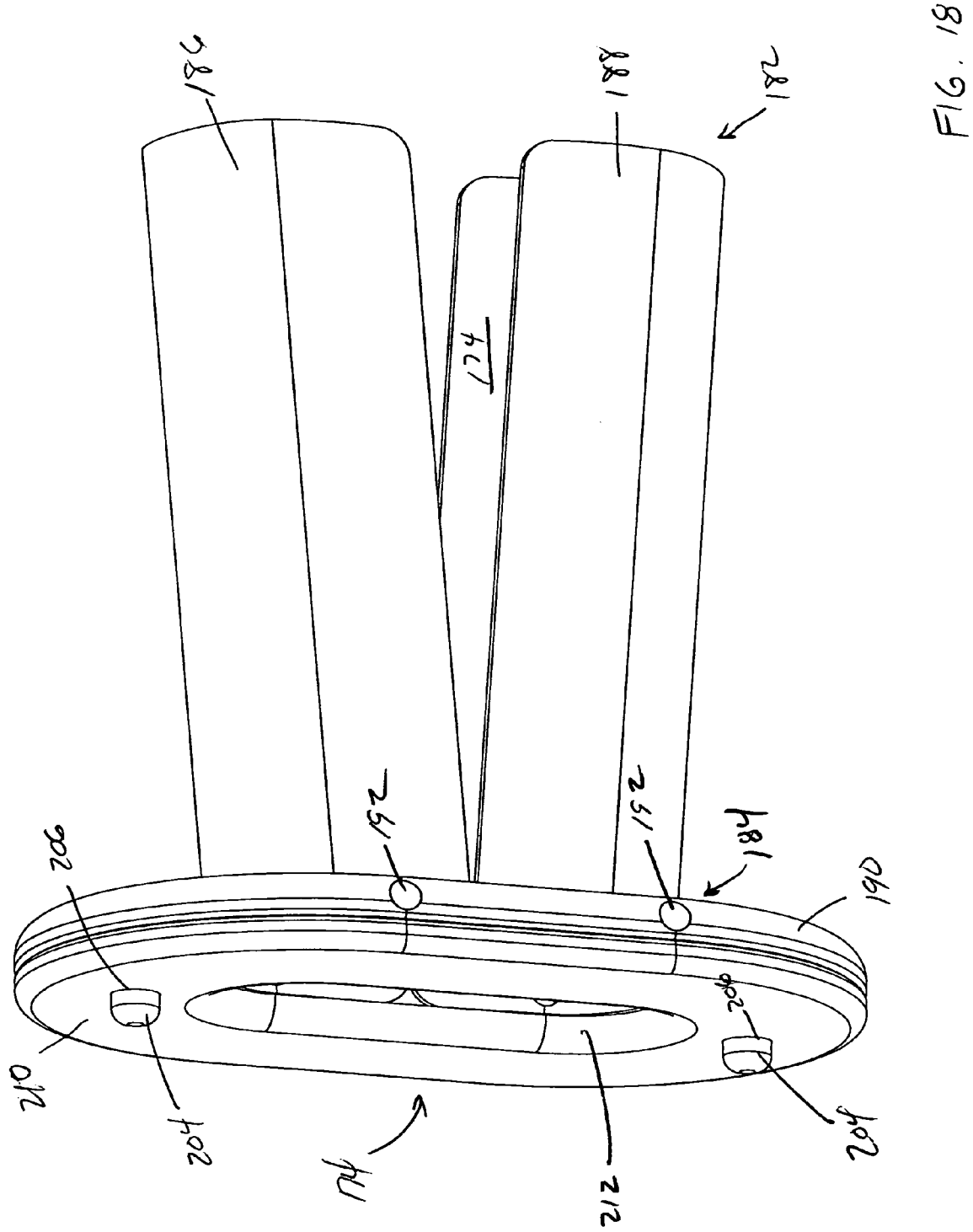
FIG. 18 is a perspective view of the outer portal member of FIG. 17.

Referring now to FIGS. 16-18, a second embodiment of an outer portal member or fourth sleeve member 118 is illustrated. In this embodiment, the outer portal member 118 generally includes a sleeve portion 170 having a first end 182 and a second end 184. The sleeve portion 170 defines an elongated aperture 174 that extends from the first end 182 to the second end 184. The second outer portal member embodiment 118 generally has similar overall width, height, and length dimensions as the first outer portal member 18 shown in FIGS. 13-15.

The sleeve portion 170 illustrated in the second embodiment, however, includes a first sleeve section 186 and a second sleeve section 188 that define the elongated aperture 174. The first and second sleeve sections 186, 188 are coupled to a flange or collar 190 at pivot locations 192. Each of the first and second sleeve sections 186, 188 is configured to rotate or pivot, relative to the collar 190, from a retracted position (shown in FIG. 16) to a distended position (shown in FIGS. 17 and 18).

The second end 184 of each of the sleeve sections 186, 188 is angled such that an inner region 194 of each section is longer than an outer region 196. In other words, the second end 184 of each section has an oblique edge construction 198 (partially shown in FIG. 16) relative to the inner and outer regions 194, 196 of the first and second sleeve sections 186, 188.

The outer portal member 118 further includes a clamp plate 210 positioned adjacent to the collar 190. Typically, the clamp plate 210 is positioned in relation to the collar 190 so that a gap G is provided between the collar 190 and the clamp plate 210. Alignment spacers 202 in cooperation with holes 206 formed in the clamp plate 210 properly orient the clamp plate 210 relative to the collar 190 so that an opening 212 in the clamp plate 210 is aligned with the elongated aperture 174 of the sleeve portion 170. The alignment spacers 202 can also be configured to maintain the gap G between the collar 190 and the clamp plate 210. For example, the alignment spacers 202 can be configured to provide a sufficient interference fit with the holes 206 formed in the clamp plate 210 such that the clamp plate 210 seats in an offset position from the collar 190 when no force is applied. In the illustrated embodiment, the spacers 202 are pegs 204 extending from a first surface 200 of the collar 190.

As shown in FIG. 16, when the gap G is provided between the collar 190 and the clamp plate 210, the first and second sleeve sections 186, 188 remain in the retracted position. In the retracted position, the outer portal member 118 can be introduced into an access opening area as previously described with respect to the first outer portal member embodiment.

When the outer portal member 118 is positioned adjacent to the spinal column area at the desired depth, and the three nested members 20, 24, 26 are removed from the elongated aperture 174, the first and second sleeve sections 186, 188 can be outwardly distended to further expose the first and second pedicle sites. In particular, the clamp plate 210 can be forcibly positioned to contact the first surface 200 of the collar 190 (FIGS. 17 and 18). As the clamp plate 210 is forced towards the collar 190, the clamp plate 210 contacts the oblique edge construction 198 of the second end 184 of the first and second sleeve sections 186, 188. The force from the clamp plate 210 pivots the first end 182 of the first and second sleeve members 186, 188 outward away from one another. That is, the second end 184 of the first and second sleeve members 186, 188 pivot about pivot locations 192, and the first end 182 of the first and second sleeve members 186, 188 rotate in opposite directions from one another.

The clamp plate 210, spacers 198, and collar 190 can be configured such that a surgeon can forcibly position the outer portal member 118 in the distended position by hand, or such that a clamp (not shown) is required to press the clamp plate 210 toward the collar 190. The pivoting design of this second outer portal member embodiment provides a greater access opening adjacent to the spinal column area without having to expand the access opening in the tissue and muscle region of the patient's back. This is advantageous in further reducing trauma in situations where access to a larger spinal column area is needed.

The above specification provides a complete description of SPINAL ACCESS INSTRUMENT. Since many embodiments of the invention can be made without departing from the spirit and scope of the invention, the invention resides in the claims hereinafter appended.

What is claimed is:

1. A surgical instrument for providing an access opening to spinal column area, the surgical instrument comprising:
   a) a first wire and a second wire for locating an access opening site;
   b) an incremental opening arrangement having a plurality of nested members, the plurality of nested members including at least:
      i) a dissector member slidably positionable over the first and second wires with the first and second wires being received within at least a portion of the dissector member, the first dissector member configured to provide an access opening at the access opening site;
      ii) a sleeve member slidably positionable over the dissector member, the sleeve member being sized and configured to expand the opening area of the access opening at the access opening site; wherein the sleeve member is a second sleeve member and the plurality of nested members further includes a third sleeve member and a fourth sleeve member, each of the nested members being configured to incrementally expand the opening area of the access opening at the access opening site.

2. The surgical instrument of claim 1, wherein the second sleeve member includes a stop structure, the second sleeve member configured to slide in a first direction relative to the dissector member until the stop structure of the second sleeve member engages the dissector member.

3. The surgical instrument of claim 2, wherein the stop structure of the second sleeve member is configured to interconnect the dissector member and the second sleeve member when the dissector member is slid in a second direction opposite the first direction.

4. The surgical instrument of claim 2, wherein the stop structure of the third sleeve member is configured to interconnect the second sleeve member and the third sleeve member when the dissector member is slid in the second direction opposite the first direction.

5. The surgical instrument of claim 3, wherein the stop structure of the second sleeve member includes pins positioned to engage shoulders of the dissector member.

6. The surgical instrument of claim 3, wherein the third sleeve member includes a stop structure, the third sleeve member being configured to slide in the first direction relative to the second sleeve member until the stop structure of the third sleeve member engages the second sleeve member.

7. The surgical instrument of claim 3, wherein the stop structure of the third sleeve member includes pins positioned to engage notches of the second sleeve member.

8. The surgical instrument of claim 1, wherein the dissector member, the second sleeve member, and the third sleeve member are slidably removable from the fourth sleeve member in a nested configuration.

9. A surgical instrument for providing an access opening to a spinal column area, the surgical instrument comprising:
   a) a first wire and a second wire for locating an access opening site;
   b) an incremental opening arrangement having a plurality of nested members, the plurality of nested members including at least:
      i) a dissector member slidably positionable over the first and second wires with the first and second wires being received within at least a portion of the dissector member, the first dissector member configured to provide an access opening at the access opening site;
      ii) a sleeve member slidably positionable over the dissector member, the sleeve member being sized and configured to expand the opening area of the access opening at the access opening site, the sleeve member including an elongated aperture configured to provide access to the spinal column area, wherein the sleeve member is an outer portal member, the elongated aperture being sized to access first and second pedicle locations at the spinal column area, wherein the outer portal member includes first and second sleeve sections selectively positionable in a retracted position and a distended position, the distended position expanding the access opening at the spinal column area.

10. The surgical instrument of claim 9, wherein each of the first and second sleeve sections of the outer portal member are coupled to a collar at a pivot location, the sleeve sections being configured to pivot outward from the retracted position to the distended position to expand the access opening at the spinal column area.

11. The surgical instrument of claim 10, wherein the outer portal member further includes a clamp plate, the clamp plate being configured to forcibly contact the first and second sleeve sections to pivot the sleeve sections outward to the distended position.

12. A surgical instrument for accessing first and second pedicle locations of a spinal column, the surgical instrument comprising:
   a) at least a first guide wire having a first end selectively positionable at one of the first and second pedicle locations;
   b) a nested arrangement slidably positionable over the first guide wire, the nested arrangement including at least:
      i) a blade member slidably positioned over the first wire with the first wire received within at least a portion of the blade member, the blade member including a blade end configured to provide an incisional opening, wherein the blade member includes at least a first through hole extending along a first edge of the blade member, the first through hole being configured for receipt of the first guide wire; and
      ii) an outer portal member configured to slide over the blade member for introduction into the incisional opening, the outer portal member having an elongated access aperture, the elongated aperture having a longitudinal dimension that corresponds to the distance between the first and second pedicle locations.

13. The surgical instrument of claim 12, wherein the elongated aperture of the outer portal member simultaneously exposes the first and second pedicle locations of the spinal column.

14. The surgical instrument of claim 12, wherein the surgical instrument includes a second guide wire, and wherein the blade member includes a second through hole extending along a second edge of the blade member, the second though hole being configured for receipt of the second guide wire.

15. The surgical instrument of claim 12, wherein the nested arrangement further includes an inner portal member positionable within the elongated access aperture of the outer portal member, the inner portal member having an inner elongated aperture for introduction into the incisional opening, the inner elongated aperture being sized to incrementally expand of the incisional opening.

16. The surgical instrument of claim 15, wherein the nested arrangement further includes an intermediate portal member positionable between the inner portal member and the outer portal member, the intermediate portal member having an intermediate elongated aperture for introduction into the incisional opening, the intermediate elongated aperture being sized to incrementally expand the incisional opening.

* * * * *